United States Patent
Hill

[11] Patent Number: 6,016,980
[45] Date of Patent: Jan. 25, 2000

[54] DISINFECTANT DEVICE FOR A GARBAGE DISPOSAL

[76] Inventor: Dominic Hill, The Coach House Town Street, Nidd, Harrogate HG3 3BN, United Kingdom

[21] Appl. No.: 09/124,921
[22] Filed: Jul. 30, 1998
[51] Int. Cl.[7] .................................................. B02C 19/00
[52] U.S. Cl. ............................................... 241/46.013
[58] Field of Search ............................. 4/DIG. 4, 294, 4/222.1, 222; 241/46.013, 46.014, 46.015

[56] References Cited

U.S. PATENT DOCUMENTS

| | | | |
|---|---|---|---|
| 4,480,795 | 11/1984 | Pellegrino | 241/46.013 |
| 4,852,813 | 8/1989 | Brackett | 241/46.013 |
| 5,577,673 | 11/1996 | McMurphy et al. | 241/46.013 |

*Primary Examiner*—Mark Rosenbaum

[57] ABSTRACT

A garbage disposal substance dispensing apparatus is provided for use with a sink basin having a faucet for supplying water and an outlet drain formed on a bottom face thereof. The outlet drain has a garbage disposal adapted to rotate upon the actuation thereof. A hollow container is provided with apertures formed therein for communicating with an interior space of the container. Situated within the container is a solid material adapted to dissolve upon being subjected to water and being agitated, as in the case wherein the ball is placed within the garbage disposal when actuated and water is supplied by the water faucet.

6 Claims, 1 Drawing Sheet

DISINFECTANT DEVICE FOR A GARBAGE DISPOSAL

BACKGROUND OF THE INVENTION

1. Field of the Invention

The present invention relates to garbage disposal treatment systems and more particularly pertains to a new disinfectant device for a garbage disposal for disinfecting a garbage disposal and further emitting a pleasant aroma therefrom.

2. Description of the Prior Art

The use of garbage disposal treatment systems is known in the prior art. More specifically, garbage disposal treatment systems heretofore devised and utilized are known to consist basically of familiar, expected and obvious structural configurations, notwithstanding the myriad of designs encompassed by the crowded prior art which have been developed for the fulfillment of countless objectives and requirements.

Known prior art garbage disposal treatment systems and the like include U.S. Pat. No. 4,852,813; U.S. Pat. No. 4,480,795; U.S. Pat. No. 5,310,096; U.S. Pat. No. 4,910,808; U.S. Pat. No. 5,423,621; and U.S. Pat. No. Des. 382,611.

In these respects, the disinfectant device for a garbage disposal according to the present invention substantially departs from the conventional concepts and designs of the prior art, and in so doing provides an apparatus primarily developed for the purpose of disinfecting a garbage disposal and further emitting a pleasant aroma therefrom.

SUMMARY OF THE INVENTION

In view of the foregoing disadvantages inherent in the known types of garbage disposal treatment systems now present in the prior art, the present invention provides a new disinfectant device for a garbage disposal construction wherein the same can be utilized for disinfecting a garbage disposal and further emitting a pleasant aroma therefrom.

The general purpose of the present invention, which will be described subsequently in greater detail, is to provide a new disinfectant device for a garbage disposal apparatus and method which has many of the advantages of the garbage disposal treatment systems mentioned heretofore and many novel features that result in a new disinfectant device for a garbage disposal which is not anticipated, rendered obvious, suggested, or even implied by any of the prior art garbage disposal treatment systems, either alone or in any combination thereof.

To attain this, the present invention is adapted for use with a sink basin with a faucet for supplying water and an outlet drain formed on a bottom face thereof. The outlet drain has a garbage disposal adapted to rotate upon the actuation thereof, as is conventional. The present invention includes a hollow spherical ball constructed from a nylon plastic material for defining an interior space. The spherical ball has a plurality of equally spaced apertures. Such apertures are formed in the ball along equally spaced, parallel concentric circles on the ball. Next provided is a solid material formed of a disinfectant substance and a perfume substance. The solid material takes the form of a sphere with a diameter slightly less than that of the spherical ball. In use, the solid material is situated within the spherical ball and adapted to dissolve upon being subjected to water and being agitated, as in the case wherein the ball is placed within the garbage disposal when actuated and water is supplied by the water faucet. When dissolved, the solid material emits a pleasant aroma along with an anti-bacterial agent for disinfecting the garbage disposal.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new disinfectant device for a garbage disposal apparatus and method which has many of the advantages of the garbage disposal treatment systems mentioned heretofore and many novel features that result in a new disinfectant device for a garbage disposal which is not anticipated, rendered obvious, suggested, or even implied by any of the prior art garbage disposal treatment systems, either alone or in any combination thereof.

It is another object of the present invention to provide a new disinfectant device for a garbage disposal which may be easily and efficiently manufactured and marketed.

It is a further object of the present invention to provide a new disinfectant device for a garbage disposal which is of a durable and reliable construction.

An even further object of the present invention is to provide a new disinfectant device for a garbage disposal which is susceptible of a low cost of manufacture with regard to both materials and labor, and which accordingly is then susceptible of low prices of sale to the consuming public, thereby making such disinfectant device for a garbage disposal economically available to the buying public.

Still yet another object of the present invention is to provide a new disinfectant device for a garbage disposal which provides in the apparatuses and methods of the prior art some of the advantages thereof, while simultaneously overcoming some of the disadvantages normally associated therewith.

Still another object of the present invention is to provide a new disinfectant device for a garbage disposal for disinfecting a garbage disposal and further emitting a pleasant aroma therefrom.

Even still another object of the present invention is to provide a new disinfectant device for use with a sink basin having a faucet for supplying water and an outlet drain formed on a bottom face thereof. The outlet drain has a garbage disposal adapted to rotate upon the actuation thereof. A hollow container is provided with apertures formed therein for communicating with an interior space of the container. Situated within the container is a solid material adapted to dissolve upon being subjected to water and being agitated, as in the case wherein the ball is placed within the garbage disposal when actuated and water is supplied by the water faucet.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
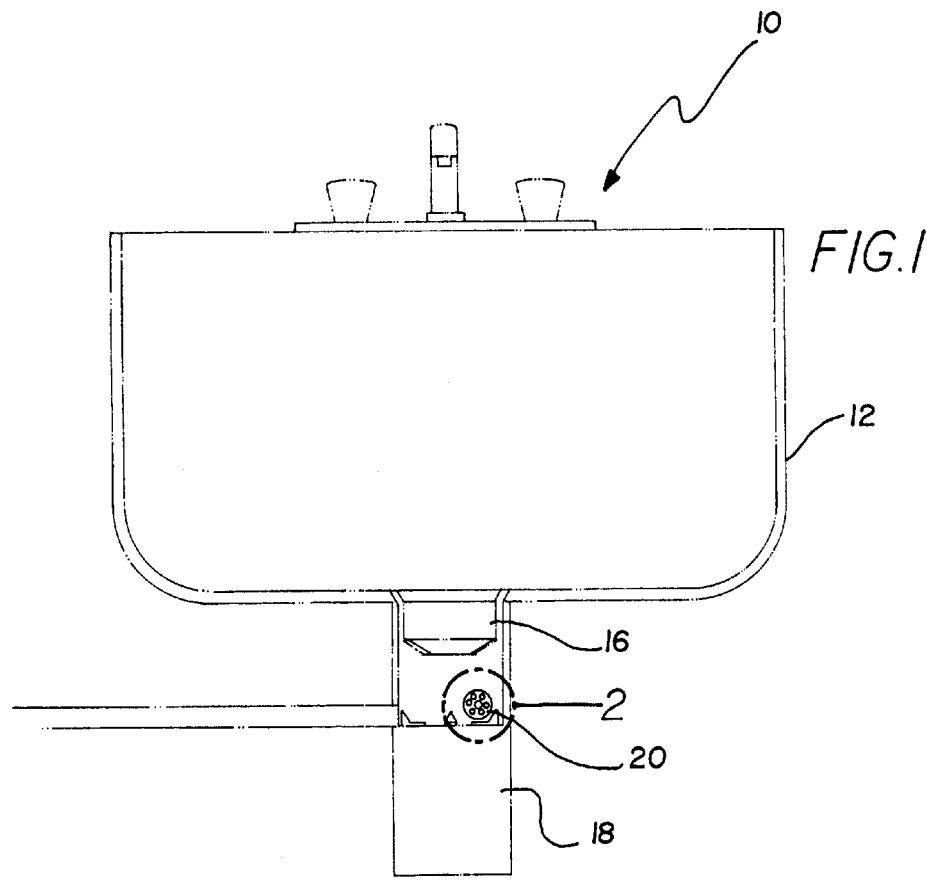
FIG. 1 is a view of a new disinfectant device for a garbage disposal according to the present invention.
Figure 2:
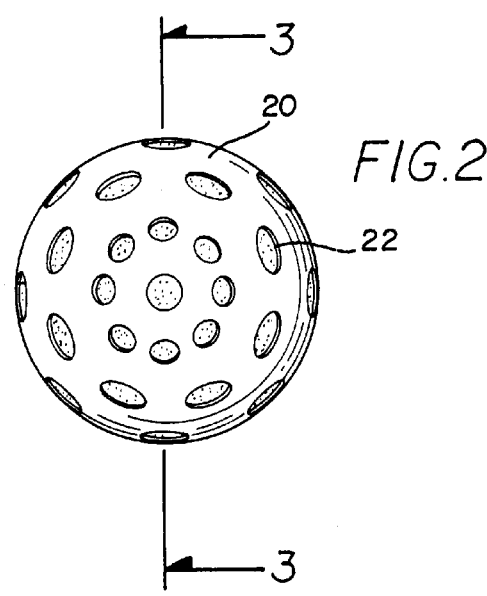
FIG. 2 is a side view of the present invention.
Figure 3:
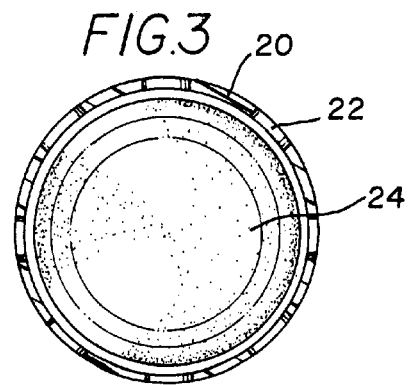
FIG. 3 is a cross-sectional view of the present invention taken along line 3—3 shown in FIG. 2.

With reference now to the drawings, and in particular to FIGS. 1 through 3 thereof, a new disinfectant device for a garbage disposal embodying the principles and concepts of the present invention and generally designated by the reference numeral 10 will be described.

The present invention, designated as numeral 10, is adapted for use with a sink basin 12 having a faucet 14 for supplying water and an outlet drain 16 formed on a bottom face thereof. The outlet drain has a garbage disposal 18 adapted to rotate upon the actuation thereof, as is conventional.

The present invention includes a hollow spherical ball 20 constructed from a nylon plastic material for defining an interior space. The spherical ball has a plurality of equally spaced apertures 22. Such apertures are formed in the ball along equally spaced, parallel concentric circles on the ball. As shown in FIG. 2, apertures formed on concentric circles of a smaller diameter may optionally have a common diameter that is smaller than those formed on concentric circles with a larger diameter. In the preferred embodiment, the spherical ball has an outer surface with a diameter of 41 mm and an inner surface with a diameter of about 38 mm.

Next provided is a solid material 24 formed of a disinfectant substance and a perfume substance. The solid material takes the form of a sphere with a diameter slightly less than that of the spherical ball. In use, the solid material is situated within the spherical ball and adapted to dissolve upon being subjected to water and being agitated, as in the case wherein the ball is placed within the garbage disposal when actuated and water is supplied by the water faucet. When dissolved, the solid material emits a pleasant aroma along with an anti-bacterial agent for disinfecting the garbage disposal. As an option, the solid material may further include a lubricating substance which is emitted during use. This would abate any noise associated with the garbage disposal while running.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A garbage disposal disinfecting system comprising, in combination:

a sink basin with a faucet for supplying water and an outlet drain formed on a bottom face thereof, the outlet drain having a garbage disposal adapted to rotate upon the actuation thereof;

a hollow container constructed from a nylon plastic material for defining an interior space, the container being formed by an exterior wall, the exterior wall having apertures extending into the interior space of the container such that the container is adapted for permitting environmental communication between the interior space of the container and an exterior environment outside the container, the container being generally spherical to prevent the container from passing through the garbage disposal and to facilitate agitation of the container by the garbage disposal when the container is positioned in the outlet drain, the spherical container having a plurality of equally spaced apertures formed therein along equally spaced, parallel concentric circles on the container; and a solid material formed of a disinfectant substance and a perfume substance, the solid material forming a ball with a diameter slightly less than that of the spherical container, the solid material being situated within the spherical container and adapted to dissolve upon being subjected to water and agitation of the container.

2. A garbage disposal substance dispensing apparatus comprising:

a sink basin with a faucet for supplying water and an outlet drain formed on a bottom face thereof, the outlet drain having a garbage disposal adapted to rotate upon activation of the garbage disposal;

a hollow container formed by an exterior wall, the exterior wall having apertures extending into an interior space of the hollow container such that the hollow container is adapted for permitting environmental communication between the interior space of the container and an exterior environment outside the hollow container, the hollow container being generally spherical to prevent the container from passing through the garbage disposal and to facilitate agitation of the container by the garbage disposal when the container is positioned in the outlet drain; and a solid material situated within the container and adapted to dissolve upon being subjected to water and agitation of the container to form a solution dispersed through the apertures in the hollow container into the outlet drain by agitation of the spherical hollow container, the solution being for cleaning the outlet drain and the garbage disposal.

3. The garbage disposal substance dispensing apparatus as set forth in claim 2 wherein the material is formed of a disinfectant substance.

4. The garbage disposal substance dispensing apparatus as set forth in claim 2 wherein the material is formed of a perfume substance.

5. The garbage disposal substance dispensing apparatus as set forth in claim 2 wherein the material is formed of a lubricating substance.

6. The garbage disposal substance dispensing apparatus as set forth in claim 2 wherein the container is constructed from a nylon plastic material.

\* \* \* \* \*